United States Patent [19]  [11] Patent Number: 4,999,283
Zavos et al.  [45] Date of Patent: Mar. 12, 1991

[54] METHOD FOR X AND Y SPERMATOZOA SEPARATION

[75] Inventors: Panayiotis M. Zavos; Karl A. Dawson, both of Lexington, Ky.

[73] Assignee: University of Kentucky Research Foundation, Lexington, Ky.

[21] Appl. No.: 396,738

[22] Filed: Aug. 18, 1989

Related U.S. Application Data

[63] Continuation of Ser. No. 818,338, Jan. 10, 1986, abandoned.

[51] Int. Cl.$^5$ .................. A01N 1/02; C12Q 1/00; C12N 5/00
[52] U.S. Cl. .................... 435/2; 435/7.21; 435/240.1; 435/240.2; 436/501; 436/503; 436/510; 436/514; 436/547; 436/548; 436/811; 436/813; 436/824; 436/906; 530/413
[58] Field of Search .............. 435/7, 2, 240.1, 240.2; 436/503, 501, 510, 519, 517, 518, 811, 813, 824, 906; 530/387, 806, 809, 413

[56] References Cited

U.S. PATENT DOCUMENTS

| | | | |
|---|---|---|---|
| 3,894,529 | 7/1975 | Shrimpton | 435/2 |
| 4,083,957 | 4/1978 | Lang | 435/2 |
| 4,276,139 | 7/1981 | Lawson | 435/2 |
| 4,448,767 | 5/1984 | Bryant | 435/2 |
| 4,511,661 | 4/1985 | Goldberg | 436/503 |
| 4,680,258 | 7/1987 | Hammerling et al. | 435/7 |

OTHER PUBLICATIONS

"H-Y Antigen: Genetics and Serology", 1977 *Immunological Review*, Wachtel.
Bennett & Boyse, "Sex Ratio in Progeny of Mice Inseminated with Sperm Treated with H-Y Antiserum".

*Primary Examiner*—Robin Teskin
*Attorney, Agent, or Firm*—King & Schickli

[57] ABSTRACT

A method for separating male and female determining spermatozoa includes the initial step of exposing freshly ejaculated spermatozoa in a substantially protein free diluent to an excess concentration of a monoclonal antibody directed against H-Y antigen that binds substantially exclusively with male determining spermatozoa. The method continues with the suspending of the exposed spermatozoa together with a conjugate of (1) an immunoglobulin G antibody that binds substantially exclusively to the monoclonal antibody and (2) an immunoabsorbant substrate in a substantially protein free diluent. This forms a conjugate/spermatozoa preparation. The method concludes with the recovering of the separated male and female determining spermatozoa.

17 Claims, 1 Drawing Sheet

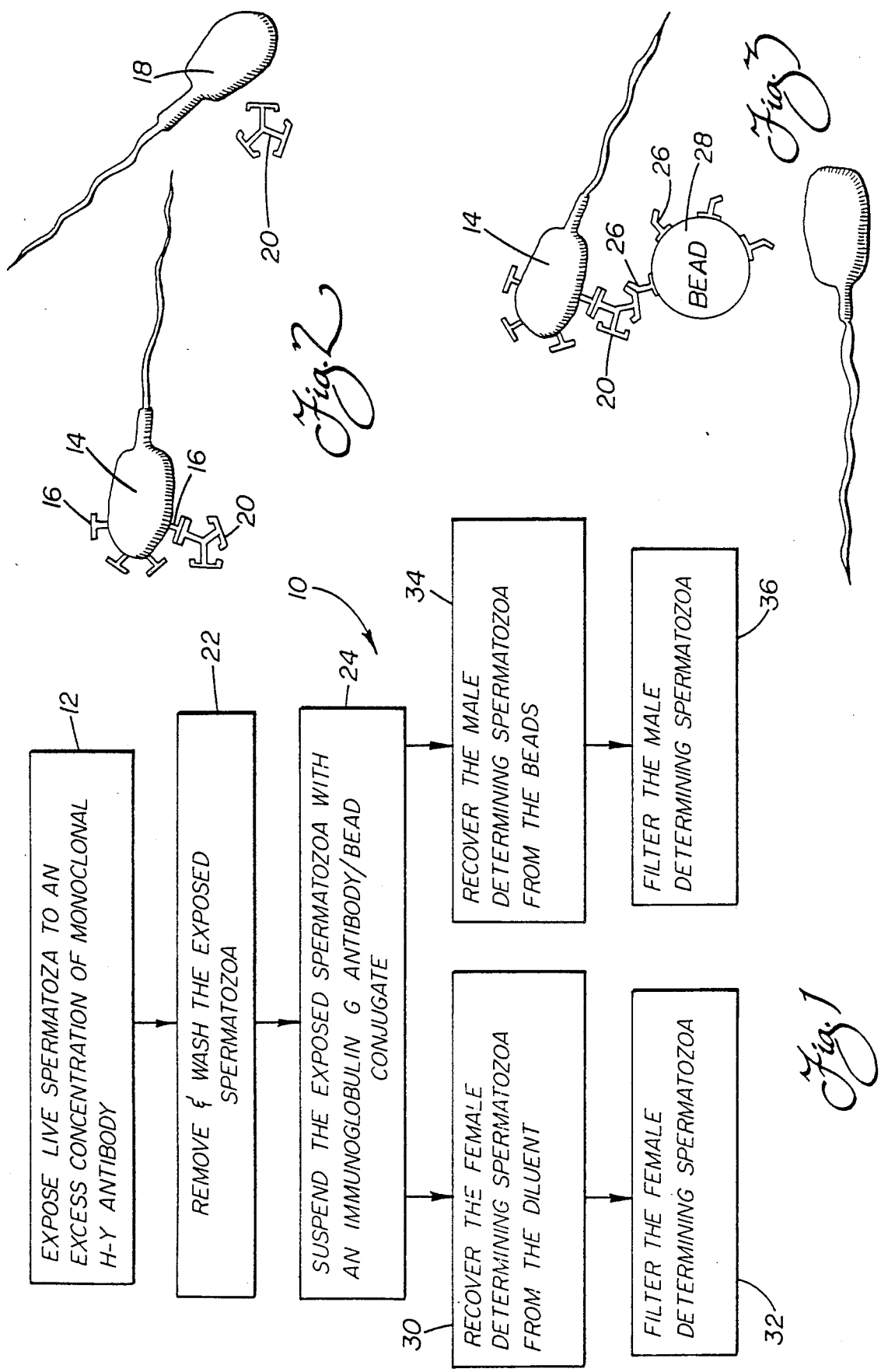

METHOD FOR X AND Y SPERMATOZOA SEPARATION

This is a continuation of application Ser. No. 818,338, filed Jan. 10, 1986 now abandoned.

TECHNICAL FIELD

This invention relates to a method for separating male and female determining spermatozoa for the purpose of selectively increasing the probability of producing offspring of either sex.

BACKGROUND OF THE INVENTION

The ability to select the sex of offspring produced in fertilization has long been recognized as having tremendous commercial potential and application. An excellent example of this may be found in the field of animal husbandry.

Dairy farm operations require the female of the species, cows, for milk production. Males of the species, bulls, are only important for breeding purposes. Thus, it is clear that any method that safely and effectively increases the production of female offspring versus male offspring would greatly benefit dairy cattle breeders and farmers and, therefore, be very valuable. Such a method would allow more effective and efficient farm operation, save money and increase farm milk production.

Of course, it should be recognized that humans may also benefit from such a method of selecting the sex of offspring. Parents could very simply satisfy their desires to have a son or daughter. This allows improved family planning, may reduce family tension and also limit family size for the benefit of all involved.

Numerous attempts have been made in the past to separate x-(male determining) and y-(female determining) bearing spermatozoa in order to determine the sex of the offspring before conception. The methods used include centrifugation, filtration, electrophoresis, immunological techniques and exposure of spermatozoa to alkaline or acidic environments.

Mechanical methods of separating male and female determining spermatozoa, based on the difference in density between the two types, are disadvantageously characterized by reduced spermatozoa survivability and by reduced viability of the surviving spermatozoa. Immunological methods of spermatozoa separation do not suffer as dramatically from these disadvantages.

U.S. pat. no. 4,448,767 to Bryant discloses two methods of immunological spermatozoa separation. The first method is a single antibody separation system wherein male specific antibody is bound to sephadex beads placed in a column. Native or unseparated spermatozoa is then added to the column. The male determining spermatozoa become bound to the male specific antibody/Sephadex bead conjugates as the female spermatozoa are eluted from the column. The male determining spermatozoa are then recovered separately.

The second method is a dual antibody separation system wherein native sperm is treated with male specific antibody. A second antibody, capable of specifically binding the male specific antibody is coupled to Sephadex beads placed in a column. The male specific antibody treated spermatozoa is then added to the column. The male determining spermatozoa become bound to the second antibody/Sephadex bead conjugates through the male specific antibody as the female spermatozoa are eluted from the column. The male determining spermatozoa are then recovered separately as in the first method.

While the two Bryant methods do serve to increase the percentage of mammalian offspring of either sex as desired, the methods are not without their disadvantages and, therefore, may be improved. Specifically, Bryant discloses a complicated technique of animal immunization with histocompatability (H-Y) antigen and multiple repeated absorptions through female spleen cells to separate and purify the male specific antibody used in the Bryant method. Despite this difficult and tedious technique, it should be appreciated that the resulting antibody is still not completely binding specific to the H-Y antigen found only in male determining and not female determining spermatozoa. Thus, it should be appreciated that a portion of the resulting male specific antibody used in Bryant could disadvantageously bind through antigens other than the y-antigen to some female determining spermatozoa. As a result, some female determining spermatozoa are bound to the Sephadex beads in the Bryant columns and eluted with the male determining spermatozoa fraction. Thus, it is clear that the highest levels of effective separation are not attainable with the Bryant method.

Bryant also disadvantageously requires the packing of a column with antibody/Sephadex bead conjugate. The column must be packed properly so that the rate of flow or spermatozoa elution is within a range allowing complete immunoreaction between the spermatozoa and the antibody of the antibody/bead conjugates. Too fast a flow rate means incomplete immunoreaction and separation and, therefore, the presence of male determining spermatozoa in the eluted female determining spermatozoa fraction. The proper packing of the column requires a great deal of preparation time and large quantities of expensive eluant or filtration solution are required to complete the separation and recover the majority of the spermatozoa from the column. This last consideration is particularly important when you consider that different eluants are typically required for each species of spermatozoa being separated. Thus, large quantities of a number of different and sometimes expensive eluants must be stored at the separation lab.

An additional problem in Bryant relates to the utilization of protein containing media for spermatozoa dilution prior to exposure of the spermatozoa to the antibody. Disadvantageously, the protein in the media retards the cross reactivity of the spermatozoa and the antibody. It is believed that the existing protein fraction in the spermatozoa diluent coats the spermatozoa covering the histocompatability H-Y antigen sites on the male determining spermatozoa and preventing antibody/antigen binding. This causes incomplete separation as, with either method in Bryant, coated male determining spermatozoa are eluted with the female determining spermatozoa.

From the above, it should be appreciated that a need exists for an improved method of immunologic spermatozoa separation.

SUMMARY OF THE INVENTION

It is, accordingly, one object of the present invention to provide a method of spermatozoa separation, based on sex determining properties, overcoming the above-described limitations and disadvantages of the prior art.

A further object of the present invention is to provide an immunological method of spermatozoa separation that is less complicated and more effective than methods of the prior art.

Still another object of the present invention is to effectively separate female and male determining spermatozoa for subsequent fertilization to produce offspring of a selected sex with an increased probability of success.

A still further object of the present invention is to provide a method of separating male and female determining spermatozoa wherein the separated spermatozoa have improved efficacy and viability.

Other objects and advantages of the present invention will become apparent as the description thereof proceeds.

In satisfaction of the foregoing objects and advantages, there is provided by this invention a method for separating male and female determining spermatozoa for the purpose of selectively increasing the probability of producing offspring of either sex during subsequent fertilization.

The method includes the step of exposing unseparated, native spermatozoa to an excess concentration of a first antibody that binds substantially exclusively with male determining spermatozoa through the H-Y surface antigen. A second antibody covalently bound to an immunoabsorbent substrate, such as agarose beads, binds substantially exclusively to the first antibody. The second antibody/immunoabsorbent conjugates are suspended together with the spermatozoa previously exposed to the first antibody in a protein-free diluent appropriate for the spermatozoa being separated. For example, bovine spermatozoa may be suspended in a solution of sodium citrate having a pH of approximately 7.2 and an osmotic pressure of approximately 325 mOsm. Following immunoreaction in suspension, the female determining spermatozoa are recovered while the male determining spermatozoa are bound to the immunoabsorbent substrate through the first and second antibodies. Lastly, if desired, the male determining spermatozoa are recovered from the substrate.

More specifically, the native spermatozoa are diluted in a protein-free diluent to a concentration of between $10 \times 10^6$ to $100 \times 10^6$ active spermatozoa per milliliter depending on the species being separated. Since the diluent is protein free, there is no coating of the surface of the spermatozoa and, more particularly, the H-Y antigen sites on the male determining spermatozoa. Thus, more effective and complete immunoreaction is assured between the first antibody and the male determining spermatozoa.

Preferably, the first antibody is a male specific monoclonal antibody directed against H-Y antigen on the male determining spermatozoa. These monoclonal antibodies, available from the National Institute of Health, are prepared by outgrowth of primary hybridomas and recovery of the cultured medium. By using monoclonal antibodies of this type, no other antibodies are present in the antisera to adversely effect or block the cross reactivity of the antibodies with the H-Y antigen on the male determining spermatozoa or to bind any other antigen such as may be found on the female determining spermatozoa. Optimum selective binding is therefore assured.

Following the exposing step, the exposed spermatozoa are separated from the excess concentration of the first antibody. This separation may be performed by gentle centrifugation that does not harm the spermatozoa. The spermatozoa are then washed to remove unreacted first antibody and resuspended in fresh protein free diluent.

Preferably, the second antibody coupled to the agarose beads is an anti-immunoglobulin antibody specific for binding with the male-specific, first antibody bound to the exposed male spermatozoa. The beads are added to the exposed spermatozoa in the protein free diluent and the bead/spermatozoa preparation is agitated to prevent the beads from settling and thereby assure complete immunoreaction between the two antibodies. Again, the protein free diluent prevents antigen "coating" that can adversely effect the cross reactivity of the second antibody with the first antibody and thereby reduce separation efficiency.

Following the suspending step, the female determining spermatozoa may be recovered by draining the bead/spermatozoa preparation solution from the agarose beads now bound to the male determining spermatozoa. The drained solution is then gently centrifuged and the undamaged female determining spermatozoa are recovered in a pellet. The female determining spermatozoa may then be resuspended in fresh protein free diluent and filtered so as to substantially remove all dead and weak spermatozoa and increase the efficacy of the collected fraction. This can done by adding the spermatozoa to a column of sephadex beads. The viable spermatozoa are then eluted from the column and collected in a protein containing medium for freezing and/or subsequent use in artificial insemination.

The male determining spermatozoa are then recovered from the agarose beads. There are many methods known in the art for such recovery. The methods include competitive inhibition using a solution of male specific antibody, enzymatic digestion of the beads and alteration of the pH or salt concentration of the diluent.

The male determining spermatozoa may then be filtered and collected as described above so as to substantially remove all dead spermatozoa and increase the overall efficacy of the fraction. Specifically, viable spermatozoa pass through the column at a substantially faster rate than dead spermatozoa and, therefore, excellent separation results are attainable.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments and, its several details are capable of modifications in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing:

FIG. 1 is a flow sheet illustrating the method of the present invention;

FIG. 2 is a schematical representation showing the monoclonal antibody directed against H-Y antigen binding with the male determining spermatozoa; and FIG. 3 is a schematical representation showing the binding of the second antibody/bead conjugates to the exposed and monoclonal H-Y antibody bound male determining spermatozoa.

DETAILED DESCRIPTION OF THE INVENTION

As shown in FIG. 1, the first step 12 of the method 10 of the present invention involves exposing live, native spermatozoa to an excess concentration of an antibody that binds substantially exclusively to male determining spermatozoa. Specifically, freshly ejaculated spermatozoa are diluted to a concentration of between $10 \times 10^6$ and $100 \times 10^6$ active spermatozoa per milliliter. The diluent used varies depending on the species of the spermatozoa being separated. Specific examples of diluents include sodium citrate solution for bovine spermatozoa, creme gel buffer for equine spermatozoa and test buffer for human spermatozoa. The diluent used, however, should be free of protein as any protein in the diluent tends to coat the spermatozoa and block the H-Y antigen binding sites on the surface of the male determining spermatozoa. Thus, by substantially eliminating this blocking the method of the present invention provides conditions for optimal cross reactivity between the antibody and antigen for the best possible immunoseparation results.

An excess concentration of the male specific antibody is contained in or added to the diluent and spermatozoa. The male specific antibody is a monoclonal anti-H-Y antibody (immunoglobulin G) prepared by outgrowth of primary hybridomas and recovered from culture medium by stepwise precipitation and dialysis. Such a monoclonal antibody is produced by the mouse lymphocyte hybrid cell line B6YD1O available from the National Institute of Health.

As shown in FIG. 2, only male determining spermatozoa 14 express the H-Y antigen 16 on their surface. The female determining spermatozoa 18 do not express the H-Y antigen believed associated with the Y or male determining chromosome. Since the monoclonal antibody 20 is absolutely specific for the H-Y antigen, it binds only to the male determining spermatozoa 14 and not any of the female determining spermatozoa 18.

Following a short incubation period for immunoreaction of, for example, 45 minutes, the spermatozoa/monoclonal H-Y antibody dilution is centrifuged in step 22 to remove (note FIG. 1) and collect the exposed spermatozoa from the diluent. The exposed spermatozoa are then washed (also step 22) using fresh, pure protein free diluent in order to remove unbound monoclonal antibody. After washing, the exposed spermatozoa are resuspended in an equal volume of protein free diluent (as used during the exposing step) substantially without the presence of unbound H-Y antibody.

Immediately thereafter, antibody/immunoabsorbent conjugates are added to the dilution so as to form a conjugate/spermatozoa suspension preparation in step 24. As shown in FIG. 3, the antibody 26 coupled to the immunoabsorbent material or agarose beads 28 binds immunoglobulin G and, therefore, binds the monoclonal anti-H-Y antibody 20 already bound to the male determining spermatozoa 14. Again, just as with the first antibody 20, the female determining spermatozoa 18 do not immunoreact with the immunoglobulin G antibody 26 bound to the beads 28.

In order for the second, immunoglobulin G antibody 26, to properly react with the monoclonal H-Y antibody 20, the immunoglobulin G antibody must be species specific for the monoclonal antibody. Thus, if spermatozoa are exposed to monoclonal H-Y antibody produced by mice lymphocyte cells as described above, the second antibody bound to the conjugate must be anti-mouse immunoglobulin G. Such a conjugate of anti-mouse immunoglobulin G and agarose beads is available from Sigma Corporation.

The anti-immunoglobulin G/agarose bead conjugate is added to the diluted spermatozoa at an approximate concentration of 0.4 milliliters of conjugate beads per milliliter of diluted spermatozoa (assuming a minimum of 0.4 milligrams of mouse immunoglobulin G may be bound and eluted from each milliliter of antibody-bound beads). The conjugate/spermatozoa preparation is incubated at approximately 37° C. and agitated to prevent the beads from settling and thereby maintain the beads and spermatozoa in physical contact for complete immunoreaction. During this time, the anti-immunoglobulin G antibody of the conjugate binds the monoclonal H-Y antibody bound to the male determining spermatozoa as shown in FIG. 3. Thus, the antibody/bead conjugate agglutinates the monoclonal antibody/male determining spermatozoa complexes.

Following immunoreaction and agglutination, the female determining spermatozoa are recovered at step 30. This step may be completed by draining the conjugate/spermatozoa preparation solution from the antibody/agarose bead conjugates now bound to the male determining spermatozoa. Since the female determining spermatozoa do not bind to the beads (note FIG. 3), the female determining spermatozoa are contained in this drained solution. The solution is then gently centrifuged to collect the female determining spermatozoa in a pellet at the bottom of the centrifuge tube without significantly adversely affecting spermatozoa viability.

A Sephadex filtering column is then prepared as is known in the art. The pelleted female determining spermatozoa are then resuspended in a diluent and added in step 32 to the filtering column. Viable spermatozoa pass through or are eluted from the column at a substantially faster rate than dead or weak spermatozoa and, therefore, excellent filtering results are obtainable. The spermatozoa eluted from the column may be collected in a protein containing medium for maintaining the spermatozoa for freezing and/or subsequent use in artificial insemination. An example of such a protein containing medium is the protein free diluent used above during the exposing and suspending steps mixed with egg yolk, 20% by volume.

The male determining spermatozoa are also recovered at step 34 from the agarose beads. There are many methods known in the art for such recovery. The methods include competitive inhibition using a solution of male specific antibody, enzymatic digestion of the beads, and alteration of the pH or salt concentration of the diluent. Following recovery, the male determining spermatozoa are filtered in step 36 through a sephadex column in the same manner as the female determining spermatozoa so as to increase the efficacy of the male determining spermatozoa fraction or sample.

The following examples are presented to further illustrate the invention, but it is not to be considered as limited thereto.

EXAMPLE 1

HY antibody is obtained by outgrowth of a monoclonal hybridoma cell culture (American Type Culture Collection, Number, B6YD10). The cell culture is grown in RPMI 1640 medium with L-Glutamine (M.A.

Bioproducts) containing 200 Units of Gentomycin per ml and supplemented with 20% fetal bovine serum. The growth environment is an incubator gassed via 5% $CO_2$ in air and maintained at 37° C. Supernatant is harvested at 48-hour intervals and frozen at $-20°$ C. environment until processing. The antibody (globulin fraction) is collected from the supernatant by precipitation with 50% saturated ammonium sulfate (3×). The ammonium sulfate is then removed via dialysis against sodium citrate diluent (SCD). During this process, globulin fractions are concentrated into a volume which is one tenth of the original culture fluid collected. The recovered globulin fractions are aliquoted into 1 ml fractions, frozen, and maintained at $-70°$ C. environment until use.

EXAMPLE 2

Bovine spermatozoa are collected by any appropriate method known in the art. The semen is collected directly into a prewarmed vessel at 37° C. and maintained at this temperature until dilution 10 to 15 minutes later. The freshly ejaculated bovine spermatozoa are diluted to $40 \times 10^6$ active spermatozoa per ml by adding an appropriate quantity of physiologically balanced sodium citrate solution at 325 m Osm/liter, pH 7.2, and free of protein. An excess concentration of 1:200 monoclonal antibody directed against HY antigen as prepared in Example 1 is then added to the diluted spermatozoa. The spermatozoa preparation is then incubated for a period of 45 minutes at 37° C. The preparation is then centrifuged for 10 minutes at 1,000 g and the spermatozoa collected in a pellet. The spermatozoa pellet is then resuspended in an equal volume of sodium citrate solution without the HY antibody. Immediately thereafter, 0.4 ml of agarose beads covalently bound with anti-mouse IgG (available from Sigma Chemical Company, St. Louis, Mo.) are added per ml of diluted spermatozoa. This spermatozoa-agarose bead suspension is then incubated for 30 minutes at 37° C. Since the beads settle to the bottom of the suspension if allowed to set for five minutes or longer, the suspension is agitated or mixed every 10 minutes to keep the sperm and beads in physical contact. At the end of the 30 minute incubation period, the sperm fraction is collected by decanting or draining the supernatant. Following collection, the sperm fraction is transferred and layered on top of a Sephadex sperm filtration column and filtered.

Actually, the column consists of three disposable plastic syringes each 1 cm in diameter and 6.5 cm high. A pad of Johns-Manville Micro-Fiber, code 112, No. 475 glass, is prepared by taking thin sheets of 3 to 4 mg fiber and folding the long fibers under to make a circle of approximately 1 cm in diameter. A pad is then gently pushed to the bottom of each syringe using a Pasteur pipet until 1 to 2 mm protrudes through the hole in the syringe. The fibers are inspected so that no holes should be evident in the syringe. Twenty g of Sephadex G 15 (40-120 particle size) are added to 100 ml of diluent, 34 g/liter, 320 mOsm osmotic pressure. The sephadex is then allowed to swell at 5° C. for 4 hours. Each syringe is filled with sodium citrate solution to the 2.5 ml level. A volume of 0.8 ml of rapidly mixing Sephadex slurry is then added to the diluent in each syringe. The Sephadex is allowed to settle for 10 minutes and then the filter is ready for use. The Sephadex column should be set at 8 mm height. More Sephadex may be added, if necessary, until the level reaches the 8 mm mark. The filters are firmly held in a vertical position and a beaker is used to catch the filtrate.

Flow rates are adjusted to approximately 0.5-0.7 ml per minute measured by the 2.5-1.5 ml markings on the syringe-filters. Fast flow rates indicate insufficient fiberglass or holes in the fiberglass pads which would allow Sephadex to pass into the collection vials. Slow flow rates, however, are caused by too much fiberglass in the pad and may result in insufficient filtering. The filters are allowed to drain to the 1 ml mark and then the filter is refilled with the diluent from a wash bottle, taking care not to disturb the Sephadex surface. The filters are allowed to drain to the 2.5 ml level and the beaker is replaced with a 20 ml volumetric flask and a 1 ml semen sample containing $40 \times 10^6$ active spermatozoa is added or layered to the top of the column. All samples are mixed immediately before sampling to assure accuracy. Adequate time is allowed for the filter to drain to 1.2 ml mark and then to be refilled to the top with additional sodium citrate solution.

Male determining spermatozoa are recovered as follows. Agarose beads recovered following draining of the female determining spermatozoa are mixed with monoclonal H-Y antibody twice the original concentration used during the female determining spermatozoa separation procedure. As it may be noted, the agarose beads at the end of the separation procedure formed complexes made out of the antibody/bead conjugate which agglutinated the monoclonal antibody/male determining spermatozoa. The added H-Y antibody in excess ($2\times$ the original concentration) is mixed gently via agitation to break the bondage of the male spermatozoa and the agarose bead. As the bondage is broken, the H-Y antibody then cross reacts with the anti-immunoglobulin G site on the agarose bead rendering it inactive (inhibited). The method via which the process of separation of the male determining spermatozoa form the bead conjugates is otherwise known as competitive inhibition. The agitation for purposes of separation of the male spermatozoa may continue for 30 minutes (at 37° C.) or until no visible physical bondage between the beads and the spermatozoa is evident. Following this, the agitated solution is allowed to sit for an additional 30 minutes to allow the beads to settle to the bottom of the container and then the supernatant is removed which would contain the freed male spermatozoa (37° C.). Following recovery the male determining spermatozoa are filtered in step 36 through a Sephadex column in the same manner as the female determining spermatozoa and processed either for artificial insemination or for cryopreservation purposes.

We claim:

1. The method for separating male and female determining spermatozoa for the purpose of controlling the sex of offspring prior to conception, comprising the steps of:

exposing the spermatozoa in a protein free diluent to an excess concentration of a first antibody that binds male determining spermatozoa;

suspending said exposed spermatozoa together with a conjugate of a second antibody that binds exclusively to said first antibody and an immunoabsorbent substrate in a protein free diluent to form a conjugate/spermatozoa preparation; and recovering the female determining spermatozoa from the conjugate/spermatozoa preparation while said male determining spermatozoa are bound to said immunoabsorbent substrate.

2. The method for separating male and female determining spermatozoa recited in claim 1, including the additional step of recovering said male determining spermatozoa from said immunoabsorbent substrate.

3. The method for separating male and female determining spermatozoa recited in claim 1, wherein said exposing step includes the additional step of diluting said spermatozoa to a concentration of between $10 \times 10^6$ and $100 \times 10^6$ active spermatozoa per milliliter of protein free diluent.

4. The method for separating male and female determining spermatozoa recited in claim 1, wherein said first antibody is monoclonal antibody directed against H-Y antigen of said male determining spermatozoa.

5. The method for separating male and female determining spermatozoa recited in claim 1, including the steps of recovering said exposed spermatozoa from said excess concentration of said first antibody and washing said exposed spermatozoa to remove unbound first antibody.

6. The method for separating male and female determining spermatozoa recited in claim 5, wherein said recovering is by centrifugation.

7. The method for separating male and female determining spermatozoa recited in claim 5, including the step of resuspending said washed, exposed spermatozoa in a protein free diluent.

8. The method for separating male and female determining spermatozoa recited in claim 1, including the additional step of incubating said spermatozoa at approximately 37° C. during said exposing and suspending steps.

9. The method for separating male and female determining spermatozoa recited in claim 1, wherein said immunoabsorbent substrate is agarose beads.

10. The method for separating male and female determining spermatozoa recited in claim 1, wherein said second antibody is anti-immunoglobulin antibody capable of binding said first antibody.

11. The method for separating male and female determining spermatozoa recited in claim 1, wherein said suspending step includes the additional step of agitating said conjugate/spermatozoa preparation to prevent the immunoabsorbent substrate from settling.

12. The method for separating male and female determining spermatozoa recited in claim 1, wherein said female determining spermatozoa recovering step includes the steps of draining said protein free diluent and female determining spermatozoa from said immunoabsorbent substrate and then centrifuging said protein free diluent and female determining spermatozoa to separate said female determining spermatozoa from said diluent.

13. The method for separating male and female determining spermatozoa recited in claim 1, including the additional step of filtering the separated female determining spermatozoa so as to substantially remove dead spermatozoa and increase overall efficacy.

14. The method for separating male and female determining spermatozoa recited in claim 13, wherein said filtering step includes the step of passing the separated female determining spermatozoa through an unbound sephadex bead column.

15. The method for separating male and female determining spermatozoa recited in claim 2, including the additional step of filtering the separated male determining spermatozoa so as to substantially remove dead spermatozoa and increase overall efficacy.

16. The method for separating male and female spermatozoa recited in claim 2, including the additional steps of separately filtering the separated male and female determining spermatozoa so as to remove dead spermatozoa and increase overall efficacy and separately collecting said separated male and female determining spermatozoa in a protein containing media following filtering, said protein containing media serving to support the separated spermatozoa until subsequent use in artificial insemination.

17. The method for separating male and female determining spermatozoa recited in claim 1, wherein said protein free diluent is a sodium citrate buffer.

* * * * *